US008869586B2

(12) United States Patent
Margalit

(10) Patent No.: US 8,869,586 B2
(45) Date of Patent: Oct. 28, 2014

(54) METHODS AND SYSTEMS FOR CALIBRATING CHEMICAL SENSORS

(75) Inventor: Mordehai Margalit, Zichron (IL)

(73) Assignee: Empire Technology Development LLC, Wilmington, DE (US)

(*) Notice: Subject to any disclaimer, the term of this patent is extended or adjusted under 35 U.S.C. 154(b) by 209 days.

(21) Appl. No.: 13/512,799

(22) PCT Filed: Feb. 8, 2012

(86) PCT No.: PCT/US2012/024250
§ 371 (c)(1),
(2), (4) Date: May 30, 2012

(87) PCT Pub. No.: WO2013/119219
PCT Pub. Date: Aug. 15, 2013

(65) Prior Publication Data
US 2013/0199261 A1    Aug. 8, 2013

(51) Int. Cl.
*G12B 13/00*    (2006.01)
(52) U.S. Cl.
USPC .......................................................... 73/1.06
(58) Field of Classification Search
USPC ................... 73/1.06, 1.02, 1.03; 702/19–22
See application file for complete search history.

(56) References Cited

U.S. PATENT DOCUMENTS

| | | | |
|---|---|---|---|
| 4,818,348 A | 4/1989 | Stetter | |
| 7,523,638 B2 | 4/2009 | Prince | |
| 7,934,412 B2 | 5/2011 | Prince | |
| 2003/0131650 A1* | 7/2003 | Bayerle et al. ............... | 73/1.06 |
| 2005/0039515 A1 | 2/2005 | Prince | |
| 2006/0229820 A1* | 10/2006 | Kemp ............................ | 702/19 |
| 2008/0195329 A1 | 8/2008 | Prince et al. | |
| 2009/0133465 A1 | 5/2009 | Prince | |
| 2009/0139299 A1 | 6/2009 | Prince | |
| 2010/0094565 A1 | 4/2010 | Prince et al. | |

FOREIGN PATENT DOCUMENTS

| | | |
|---|---|---|
| AU | 2003263285 A1 | 2/2004 |
| CA | 2476902 | 2/2005 |
| CA | 2675173 | 7/2008 |
| FR | 2842595 | 1/2004 |
| JP | 20053002377 A | 10/2005 |
| JP | 2006300743 A | 11/2006 |
| WO | WO2004010085 A1 | 1/2004 |
| WO | WO2008/086606 A1 | 7/2008 |

OTHER PUBLICATIONS

Besnainou et al., FR2842595, Maintenance method of measurement sensor and detector for the implementation process, Jan. 29, 2004 (Machine translation).*
International Search Report and Written Opinion for PCT/US2012/024250 dated Mar. 13, 2012.

* cited by examiner

Primary Examiner — Peter Macchiarolo
Assistant Examiner — Anthony W Megna Fuentes
(74) Attorney, Agent, or Firm — Pepper Hamilton LLP

(57) ABSTRACT

Methods and systems for calibrating a chemical sensing system are disclosed. Detection of a substance using a first chemical sensor in a chemical sensing system may be initiated at a first time. The first chemical sensor may output a first sensor value. Detection of the substance using a second chemical sensor in a chemical sensing system may be initiated at a second time that differs from the first time by a delta value. The second chemical sensor may output a second sensor value. The chemical sensing system may be calibrated based on the first and second sensor values at the second time and the first and second sensor values at a current time.

29 Claims, 3 Drawing Sheets

METHODS AND SYSTEMS FOR CALIBRATING CHEMICAL SENSORS

CLAIM OF PRIORITY

This application is a U.S. national stage filing under 35 U.S.C. §371 of International Application No. PCT/US2012/24250 filed Feb. 8, 2012 entitled "Methods and Systems for Calibrating Chemical Sensors," the disclosure of which is incorporated by reference in its entirety.

BACKGROUND

Chemical sensors are used in a wide variety of environments to detect gasses or other substances for a variety of reasons. For example, chemical sensors can be used to detect whether a chemical leak has occurred in an industrial plant, the presence of a chemical substance in a fluid, the presence of radon gas in a dwelling or other structure, or the like.

The operation of a chemical sensor changes over time as a result of the exposure to such environmental conditions. As a result, the credibility of the sensor's measurement degrades over time requiring the sensor to be replaced intermittently. Such replacement is costly because of the cost of the sensors as well as the cost of human personnel required to perform such replacement.

SUMMARY

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

In an embodiment, a method of calibrating a chemical sensing system that detects a presence of a substance may include, at a first time, activating a first chemical sensor that is configured to provide sensor values responsive to the presence of the substance such that the first chemical sensor is configured to detect the substance when active. The method may further include, at a second time that is subsequent to the first time,.activating a second chemical sensor that is configured to provide sensor values responsive to the presence of the substance such that the second chemical sensor is configured to detect the substance when active and determining, by a processing device, the first sensor value associated with the first chemical sensor and a second sensor value associated with the second chemical sensor. The first sensor value and the second sensor value may be obtained at the second time. The method may further include, at a third time that is subsequent to the first time and the second time, determining, by the processing device, a third sensor value associated with the first chemical sensor and determining, by the processing device, a fourth sensor value associated with the second chemical sensor. The method may also include determining, by the processing device, a calibration value based on the first sensor value, the second sensor value, the third sensor value, and the fourth sensor value.

In an embodiment, a method of calibrating a chemical sensing system includes initiating detection of a substance using a plurality of chemical sensors in a chemical sensing system, where each of the plurality of chemical sensors outputs an associated sensor value and each of the plurality of chemical sensors initiates detection of the substance at a different time, and calibrating the chemical sensing system based on two or more sensor values at a current time and two or more sensor values at the time at which one of the chemical sensors is initiated that detects a presence of a substance may include, at a first time, activating a first of a plurality of chemical sensors, there each of the plurality of chemical sensors is configured to provide sensor value values responsive to the presence of the substance when active. The method may also include, at a second time that is subsequent to the first time, activating a second of the plurality of chemical sensors, determining, by a processing device, a first sensor value associated with the first chemical sensors, and determining, by the processing device, a second sensor value associated with the second of the plurality of chemical sensors. The first sensor value and the second sensor value are obtained at the second time. The method may further include, at a third time that is subsequent to the first time and the second time, determining, by the processing device, a third sensor value associated with the first of the plurality of chemical sensors and determining, by the processing device, a fourth sensor value associated with the second of the of the plurality of chemical sensors. The method may also include determining, by the processing device, a calibration value based on each first sensor value, each second sensor value, each third sensor value, and each fourth sensor value.

In an embodiment, a system for detecting a substance may include a first chemical sensor configured to provide sensor values responsive to a presence of the substance when the first chemical sensor is activated at a first time. The first chemical sensor may be continuously operable to detect the substance when active. The system may further include a second chemical sensor configured to provide sensor values responsive to the presence of the substance when the second chemical sensor is activated at a second time that is subsequent to the first time. The second chemical sensor may be continuously operable to detect the substance when active. The system may further include a processing device in operable communication with the first chemical sensor and the second chemical sensor. The processing device may be configured to determine a first sensor value associated with the first chemical sensor at the second time and a second sensor value associated with the second chemical sensor at the second time. The first sensor value and the second sensor value are obtained at the second time. The processing device may further be configured to determining a third sensor value associated with the first chemical sensor and a fourth sensor value associated with the second chemical sensor at a third time that is subsequent to the first time and the second time and determine a calibration value based on the first sensor value, the second sensor value, the third sensor value, and the fourth sensor value.

DETAILED DESCRIPTION

This disclosure identifies methods and systems for calibrating a chemical sensing system and maintaining calibration of the chemical sensing system over time. Such methods and systems include a plurality of chemical sensors, where each chemical sensor is initiated at a time that differs from the initiation time of the other chemical sensors in the plurality of chemical sensors. As such, while each chemical sensor undergoes degradation in the same manner as common sensors, the amount of degradation of each chemical sensor differs from each other chemical sensor since the starting times differ. The difference in initiation time between sensors can be used to provide a time independent baseline value for calibration of a chemical sensing system as further disclosed below.

As a result of using multiple chemical sensors as described herein and in equivalent ways, it is possible to extend the life of each chemical sensor and reduce the total consumption of chemical sensors in a chemical sensing system. As such, the teachings of the present disclosure may result in less cost with respect to the use of chemical sensors that are required to be replaced over time.

Figure 1:
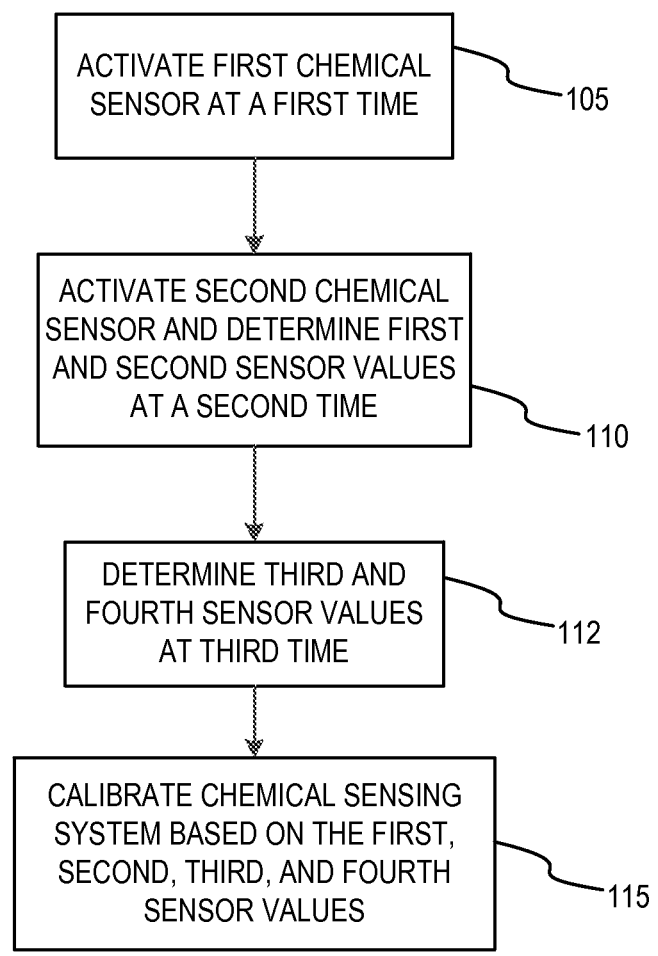
FIG. 1 depicts a flow diagram for an illustrative method of calibrating a chemical sensing system according to an embodiment.

FIG. 1 depicts a flow diagram for an illustrative method of calibrating a chemical sensing system according to an embodiment. As shown in FIG. 1, detection of a substance may be initiated by activating 105 a first chemical sensor in a chemical sensing system at a first time. The first chemical sensor may output one or more values to a processing device.

Detection of the substance may also be initiated upon activation 110 of a second chemical sensor in a chemical sensing system at a second time that differs from the first time by a delta value, Dt. The second chemical sensor may output one or more sensor values to the processing device. In addition, at the second time, the processing device may determining a first sensor value from the first chemical sensor and a second sensor value from the second chemical sensor when each respective chemical sensor outputs a sensor value at that time, as described herein. At a third time, such as, for example, a current time (a time that is subsequent to the first and second times), the processing device may determine 112 a third sensor value from the first chemical sensor and a fourth sensor value from the second chemical sensor when each respective chemical sensor outputs a sensor value at that time.

The first and second sensor values may correspond to readings with respect to the substance that the first and second chemical sensors, respectively, are configured to detect. In an embodiment, the substance may include one or more of the following substances: ammonia, arsine, butane, carbon monoxide, chlorine gas, chlorine dioxide, chloroethane, dibrorane, diisopropyl methylphosphonate, dimethyl methylphosphonate, ethylene oxide, formaldehyde, heptaflouropropane, hydrogen, hydrogen chloride, hydrogen cyanide, hydrogen fluoride, hydrogen peroxide, hydrogen sulfide, methyl salicylate, natural gas, nitric oxide, nitrogen dioxide, ozone, phosgene, propane, radon, sulfur dioxide, sulfur hexafluoride, and vinyl chloride. Additional and/or alternate substances may also be detected using chemical sensors within the scope of this disclosure.

The chemical sensing system may be calibrated 115 based on the first and second sensor values at the second time, and the third and fourth sensor values at the third time by determining a calibration value, as described in greater detail herein. In an embodiment, each of the first and second sensor values may degrade over time according to a function describing the sensor degradation, f(t). In an embodiment, the sensor degradation function, f(t), may be monotonically increasing.

In an embodiment, the first and second chemical sensors may degrade over time with an exponential trajectory (i.e., according to an exponential function). If the sensors react to substantially the same environmental conditions, such as humidity, temperature and the like, the first and second sensor values would have the same bias as a typical sensor and as each other except that the two sensors would be separated by a time Dt. For example, if a device includes both the first chemical sensor and the second chemical sensor, the chemical sensors may degrade along substantially the same trajectory. Similarly, the chemical sensors would also degrade according to substantially the same function if the first chemical sensor and the second chemical sensor are in separate devices that are substantially exposed to the same environment. Additional and/or alternate locations for the chemical sensors are also considered within the scope of this disclosure.

Based on the degradation function, the reading for the first chemical sensor, which is denoted herein as $R1$, may be determined based on the following equation: $R1=f(t+Dt)=e^{-(t+Dt)}$. Likewise, the reading for the second chemical sensor, which is denoted herein as $R2$, may correspond to the following equation: $R2=f(t)=e^{-t}$. Although the embodiment disclosed herein identifies an exponential degradation function, other degradation functions may be possible and are considered to be within the scope of this disclosure.

The difference between the first sensor value and the second sensor value may then be determined as follows:

$$R1-R2=e^{-t}e^{-Dt}-e^{-t}=e^{-t}(e^{-DT}-1).$$

A delta factor, A, may then be denoted by the following: $A=e^{-DT}-1$. Because the delta value, Dt, is a constant value, A is likewise a constant value. The value for A may be determined by recording the first and second sensor values at the initiation of the second sensor (i.e., $A=e^{-Dt}-1=R1(Dt)-R2(0)$).

Assuming that the sensor value produced by a chemical sensor having zero degradation is $R0$, then the sensor value for the first chemical sensor may be determined using the following formula: $R1(t)=R0(t)*f(t)$, where f(t) is the sensor degradation function. Similarly, the difference between the sensor values for the first and second chemical sensors may be determined using the following formula: $R1(t)-R2(t)=A*f(t)$, where A is known.

Based on the above formulae, a calibration value, $R0(t)$, may be determined by the following equation substitutions:

$$R0(t) = \frac{R1(t)}{f(t)};$$

$$f(t) = \frac{R1(t)-R2(t)}{A} = \frac{R1(t)-R2(t)}{R1(Dt)-R2(0)}; \text{ and}$$

$$R0(t) = \frac{R1(t)*(R1(Dt)-R2(0))}{R1(t)-R2(t)},$$

where the calibration value, $R0(t)$, does not suffer from sensor degradation.

In an embodiment, chemical sensors arranged according to the presently described embodiment may be used to detect the substance from the atmosphere surrounding the chemical sensing system. In an alternate embodiment, chemical sensors may be used to detect the substance in a fluid.

Figure 2:
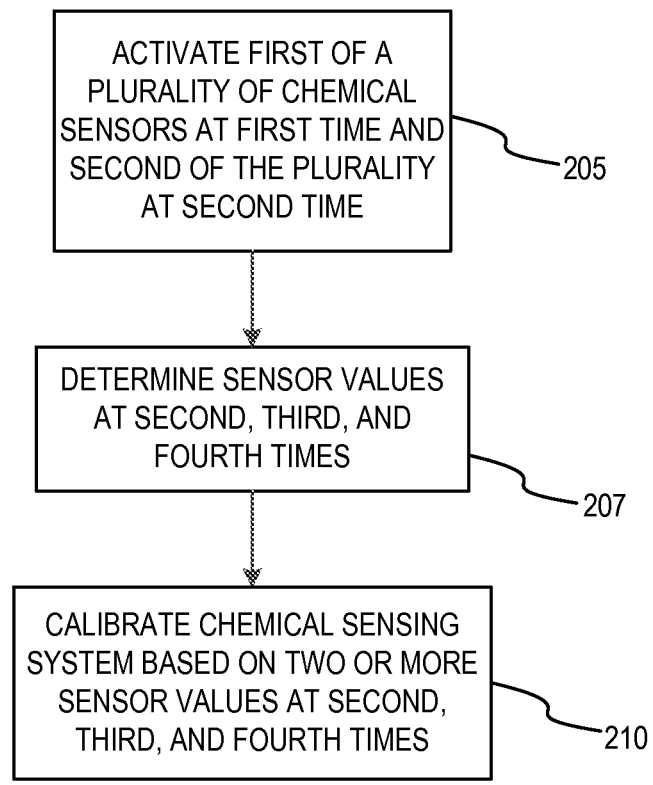
FIG. 2 depicts a flow diagram for an alternate illustrative method of calibrating a chemical sensing system according to an embodiment.

FIG. 2 depicts a flow diagram for an alternate illustrative method of calibrating a chemical sensing system according to an embodiment. As shown in FIG. 2, detection of a substance may be initiated by activating 205 a plurality of chemical sensors in a chemical sensing system. Each of the plurality of chemical sensors may output an associated sensor value, which can be determined by a processing device at a particular time, as described in greater detail herein. In addition, each of the plurality of chemical sensors may be activated 205 for detection of the substance at different times.

The sensor values may correspond to readings with respect to the substance that the associated chemical sensors are configured to detect. In an embodiment, the substance may include one or more of the following substances: ammonia, arsine, butane, carbon monoxide, chlorine gas, chlorine dioxide, chloroethane, dibrorane, diisopropyl methylphosphonate, dimethyl methylphosphonate, ethylene oxide, formaldehyde, heptaflouropropane, hydrogen, hydrogen chloride, hydrogen cyanide, hydrogen fluoride, hydrogen peroxide, hydrogen sulfide, methyl salicylate, natural gas, nitric oxide, nitrogen dioxide, ozone, phosgene, propane, radon, sulfur dioxide, sulfur hexafluoride, and vinyl chlorine. Additional and/or alternate substances may also be detected using chemical sensors within the scope of this disclosure.

The chemical sensing system may be calibrated 210 based on two or more sensor values at a third time, and two or more sensor values at a time at which one of the chemical sensors is initiated by determining a calibration value, as described in greater detail herein. Each of the sensor values may degrade over time according to a function describing the sensor degradation, f(t). In an embodiment, the sensor degradation function, f(t), may be monotonically increasing.

In an embodiment, the chemical sensors may degrade over time with an exponential trajectory (i.e., according to an exponential function). If the chemical sensors react to substantially the same environmental conditions, such as humidity, temperature and the like, each sensor value would have the same bias as a typical chemical sensor and as the sensor value for the other chemical sensor except that each pair of chemical sensors would have been initiated at a separate time identified by a delta time value, Dt, which may be a different value for each pair of chemical sensors. As a result, the degradation of each chemical sensor as identified by its degradation function would differ from the other chemical sensor by ±Dt. For example, if a device includes two chemical sensors, the chemical sensors may degrade along substantially the same trajectory because the environmental conditions would be substantially the same. Similarly, a pair of chemical sensors may degrade according to substantially the same function if the chemical sensors are in separate devices that are exposed to substantially the same environmental conditions. Additional and/or alternate locations for chemical sensors are also considered within the scope of this disclosure.

Determining a value for $R_0(t)$ may be performed according to the above disclosed equations for each pair of chemical sensors. Alternate methods of determining calibration values between more than two chemical sensors may also be performed within the scope of this disclosure according to the principles described herein.

In an embodiment, chemical sensors arranged according to the presently described embodiment may be used to detect the substance from the atmosphere surrounding the chemical sensing system. In an alternate embodiment, chemical sensors may be used to detect the substance in a fluid.

Figure 3B:
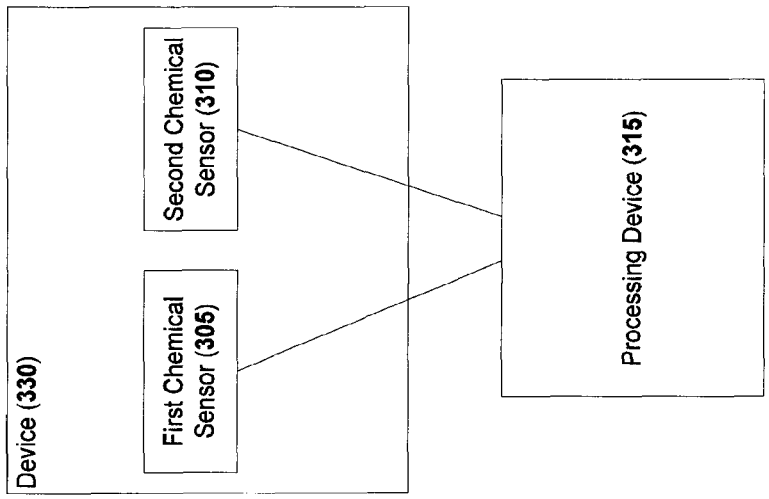
FIGS. 3A and 3B depict block diagrams for illustrative systems for detecting a substance according to embodiments.
Figure 3A:
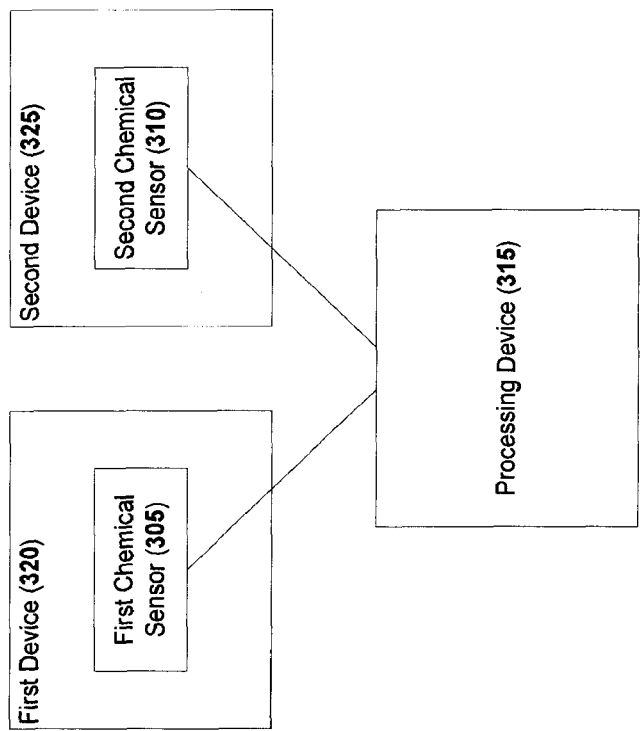

FIGS. 3A and 3B depict block diagrams for illustrative systems for detecting a substance according to embodiments. As shown in FIGS. 3A and 3B, a system for detecting a substance may include a first chemical sensor 305, a second chemical sensor 310 and a processing device 315. The first chemical sensor 305 is configured to initiate detection of the substance and output one or more sensor values to the processing device, and the second chemical sensor 310 is configured to initiate detection of the substance and output one or more second sensor values to the processing device. The substance detected by the first chemical sensor 305 and the second chemical sensor 310 may include one or more of the following: ammonia, arsine, butane, carbon monoxide, chlorine gas, chlorine dioxide, chloroethane, dibrorane, diisopropyl methylphosphonate, dimethyl methylphosphonate, ethylene oxide, formaldehyde, heptaflouropropane, hydrogen, hydrogen chloride, hydrogen cyanide, hydrogen fluoride, hydrogen peroxide, hydrogen sulfide, methyl salicylate, natural gas, nitric oxide, nitrogen dioxide, ozone, phosgene, propane, radon, sulfur dioxide, sulfur hexafluoride, and vinyl chlorine. Additional and/or alternate substance may also be detected by the first chemical sensor 305 and the second chemical sensor 310 within the scope of this disclosure.

Each of the first chemical sensor 305 and the second chemical sensor 310 may degrade over time with an exponential trajectory. For example, each of the first chemical sensor 305 and the second chemical sensor 310 may degrade according to a degradation function, such as f(t), which is disclosed above in reference to FIG. 1, or any other degradation function.

In an embodiment, each of the first chemical sensor 305 and the second chemical sensor 310 may be further configured to detect the substance in the atmosphere surrounding the system. In an alternate embodiment, each of the first chemical sensor 305 and the second chemical sensor 310 may be further configured to detect the substance in a fluid.

The processing device 315 may be in operable communication with the first chemical sensor 305 and the second chemical sensor 310. The processing device 315 may be configured to determine a calibration value based on sensor values received from the first chemical sensor 305 and the second chemical sensor 310 at the second time and sensor values from the first chemical sensor and the second chemical sensor at a third time. For example, the processing device 315 may determine a calibration value in accordance with the principles disclosed above in more detail in reference to FIG. 1. In an embodiment, the processing device 315 may be configured to determine the calibration value by determining the ratio of (i) the product of the first sensor value at the third time and the difference between the first sensor value at the second time and the second sensor value at the second time and (ii) the difference between the first sensor value at the third time and the second sensor value at the third time. Alternate methods of determining a calibration value may also be disclosed within the scope of this disclosure.

As shown in FIG. 3A, a first device 320 may include the first chemical sensor 305, and a second device 325 may include the second chemical sensor 310. In an embodiment, the processing device 315 may be part of the first device 320. In an alternate embodiment, the processing device 315 may be part of the second device 325. In an alternate embodiment, the processing device 315 may be a separate device from the first device 320 and the second device 325.

Alternately, as shown in FIG. 3B, a device 330 may include both the first chemical sensor 305 and the second chemical sensor 310. In an embodiment, the device 330 may further include the processing device 315. In an alternate embodiment, the processing device 315 may be separate from the device 330.

Program instructions, software or interactive modules for providing the interface and performing any querying or analysis associated with one or more data sets may be stored in a memory device, such as Random Access Memory (RAM) and/or Read Only Memory (ROM). Optionally, the program instructions may be stored on a tangible computer readable medium such as a compact disk, a digital disk, flash memory, a memory card, a USB drive, an optical disc storage medium, such as a Blu-ray™ disc, and/or other non-transitory storage media. For example, program instructions may be stored in a memory device or other tangible storage medium that perform one or more of the calibration processes described above in reference to FIGS. 1 and 2 and/or other similar processes. The programming instructions may be part of or in operable communication with processing device 315.

EXAMPLE 1

Sensor System for Detecting a Gas

A sensor system for detecting gasses includes two or more chemical sensors. Each chemical sensor is replaced at a different time. The sensor system is installed in a fixed location in order to detect a gas. For example, such a system can be installed in a dwelling as a means to detect radon gas. Such a system can also be installed in a public area to detect a hazardous substance. Alternately, such a system can be installed in a manufacturing facility to detect a chemical leak. The sensor system detects the gas by identifying the presence of the gas via the chemical sensors. A processing device that is in operable communication with the sensor system determines a calibration value for the sensor system based on sensor values at the current (for example, a third) time and at a time when at least one of the chemical sensors was installed (for example, a second time), and identifies whether the gas is present based on a deviation in the sensor values away from this calibration value.

EXAMPLE 2

Mobile Sensor System

A sensor system includes a plurality of cell phones, laptops or other mobile devices each having an installed chemical sensor. The chemical sensors are installed on, for example, USB sticks or other media that are connected to or inserted into the mobile devices. Each mobile device communicates with a processing device via telecommunication mechanisms installed in the mobile device in order to connect to various networks. For example, the devices can communicate with the processing device via a wireless network, a cellular network, or the like. Each mobile device transmits information received from the sensor to the processing device. In some cases, the information for the initiation of a particular sensor in a particular mobile device can be stored in the processing device. Alternately, the mobile device can locally store information pertaining to the initiation of its sensor and transmit such information to the processing device. A position for the mobile device is determined based on known methods, such as global positioning satellite (GPS) coordinates or triangulation of cell phone towers. The processing device determines a calibration value for a particular location based on sensor information received from mobile devices at the location and the respective initiation information for each mobile device.

EXAMPLE 3

Sensor System for Detecting Contaminated Fluids

A sensor system for detecting contaminated fluids includes two or more chemical sensors. Each chemical sensor is replaced at a different time. The sensor system is installed in a fixed location in order to detect elements within the fluid. For example, such a system can be installed in a manufacturing plant in order to determine whether a level of a particular substance is exceeded during a manufacturing step. Alternately, such a system could be installed in a waste water treatment plant to determine whether excessive levels of a hazardous contaminant is present in waste water before the waste water is returned to the environment. The sensor system detects the contaminating substance in the fluid by identifying the presence of the contaminating substance via the chemical sensors. A processing device that is in operable communication with the sensor system determines a calibration value for the sensor system based on sensor values at the current time (for example, a third time) and at a time when at least one of the chemical sensors was installed (for example, a second time), and identifies whether the contaminating substance is present based on a deviation in the sensor values away from this calibration value.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of calibrating a chemical sensing system that detects a presence of a substance, the method comprising:
   at a first time, activating a first chemical sensor that is configured to provide sensor values responsive to the presence of the substance such that the first chemical sensor is configured to detect the substance when active;
   at a second time that is subsequent to the first time:
      activating a second chemical sensor that is configured to provide sensor values responsive to the presence of the substance such that the second chemical sensor is configured to detect the substance when active, and
      determining, by a processing device, a first sensor value associated with the first chemical sensor and a second sensor value associated with the second chemical sensor, wherein the first sensor value and the second sensor value are obtained at the second time;
   at a third time that is subsequent to the first time and the second time:
      determining, by the processing device, a third sensor value associated with the first chemical sensor, and
      determining, by the processing device, a fourth sensor value associated with the second chemical sensor; and
   determining, by processing device, a calibration value based on the first sensor value, the second sensor value, the third sensor value, and the fourth sensor value.

2. The method of claim 1, wherein activating the first chemical sensor comprises activating the first chemical sensor located in a first device, and wherein activating the second chemical sensor comprises activating the second chemical sensor located in a second device.

3. The method of claim 1, wherein activating the first chemical sensor and activating the second chemical sensor comprise activating the first chemical sensor and activating the second chemical sensor in a device comprising the first chemical sensor and the second chemical sensor.

4. The method of claim 1, wherein activating the first chemical sensor comprises activating the first chemical sensor that is configured to provide sensor values responsive to the presence of a substance comprising one or more of the following: ammonia, arsine, butane, carbon monoxide, chlorine gas, chlorine dioxide, chloroethane, diborane, diisopropyl methylphosphonate, dimethyl methylphosphonate, ethylene oxide, formaldehyde, heptaflouropropane, hydrogen, hydrogen chloride, hydrogen cyanide, hydrogen fluoride, hydrogen peroxide, hydrogen sulfide, methyl salicylate, natural gas, nitric oxide, nitrogen dioxide, ozone, phosgene, propane, radon, sulfur dioxide, sulfur hexafluoride, and vinyl chlorine.

5. The method of claim 1, wherein activating the first chemical sensor comprises activating the first chemical sensor in an atmosphere comprising the substance.

6. The method of claim 1, wherein activating the first chemical sensor comprises activating the first chemical sensor in a fluid comprising the substance.

7. The method of claim 1, wherein determining the calibration value comprises determining via the following equation:

$$R0(t) = \frac{R1(t) \times (R1(Dt) - R2(0))}{R1(t) - R2(t)},$$

wherein R0(t) is the calibration value, R1(t) is the third sensor value at the third time, R1(Dt) is the first sensor value at the second time, R2(0) is the second sensor value at the second time, and R2(t) is the fourth sensor value at the third time.

8. The method of claim 1, wherein activating the first chemical sensor comprises connecting the first chemical sensor to a mobile device configured to communicate with the processing device.

9. The method of claim 1, wherein activating the second chemical sensor comprises connecting the second chemical sensor to a mobile device configured to communicate with the processing device.

10. The method of claim 1, wherein activating the second chemical sensor comprises activating the second chemical sensor that is configured to provide sensor values responsive to the presence of a substance comprising one or more of the following: ammonia, arsine, butane, carbon monoxide, chlorine gas, chlorine dioxide, chloroethane, dibrorane, diisopropyl methylphosphonate, dimethyl methylphosphonate, ethylene oxide, formaldehyde, heptaflouropropane, hydrogen, hydrogen chloride, hydrogen cyanide, hydrogen fluoride, hydrogen peroxide, hydrogen sulfide, methyl salicylate, natural gas, nitric oxide, nitrogen dioxide, ozone, phosgene, propane, radon, sulfur dioxide, sulfur hexafluoride, and vinyl chlorine.

11. The method of claim 1, wherein activating the second chemical sensor comprises activating the second chemical sensor in an atmosphere comprising the substance.

12. The method of claim 1, wherein activating the first chemical sensor comprises activating the first chemical sensor in a fluid comprising the substance.

13. A method of calibrating a chemical sensing system that detects a presence of a substance, the method comprising:
at a first time, activating a first of a plurality of chemical sensors, where each of the plurality of chemical sensors is configured to provide sensor values responsive to the presence of the substance when active;
at a second time that is subsequent to the first time:
activating a second of the plurality of chemical sensors;
determining, by a processing device, a first sensor value associated with the first chemical sensors; and
determining, by the processing device, a second sensor value associated with the second of the plurality of chemical sensors, wherein the first sensor value and the second sensor value are obtained at the second time;
at a third time that is subsequent to the first time and the second time:
determining, by the processing device, a third sensor value associated with the first of the plurality of chemical sensors, and
determining, by the processing device, a fourth sensor value associated with the second of the of the plurality of chemical sensors; and
determining, by the processing device, a calibration value based on each first sensor value, each second sensor value, each third sensor value, and each fourth sensor value.

14. The method of claim 13, wherein activating the first of the plurality of chemical sensors comprises activating the first of the plurality of chemical sensors located in a first device, and wherein activating the second of the plurality of chemical sensors comprises activating the second of the plurality of chemical sensor located in a second device.

15. The method of claim 13, wherein activating the plurality of chemical sensors comprises activating the plurality of chemical sensors in a device comprising each of the plurality of chemical sensors.

16. The method of claim 13, wherein activating the plurality of chemical sensors comprises activating a plurality of chemical sensors that are configured to provide sensor values responsive to the presence of a substance comprising one or more of the following: ammonia, arsine, butane, carbon monoxide, chlorine gas, chlorine dioxide, chloroethane, dibrorane, diisopropyl methylphosphonate, dimethyl methylphosphonate, ethylene oxide, formaldehyde, heptaflouropropane, hydrogen, hydrogen chloride, hydrogen cyanide, hydrogen fluoride, hydrogen peroxide, hydrogen sulfide, methyl salicylate, natural gas, nitric oxide, nitrogen dioxide, ozone, phosgene, propane, radon, sulfur dioxide, sulfur hexafluoride, and vinyl chlorine.

17. The method of claim 13, wherein activating the plurality of chemical sensors comprises activating the plurality of chemical sensors in an atmosphere comprising the substance.

18. The method of claim 13, wherein activating the plurality of chemical sensors comprises activating the plurality of chemical sensors in a fluid comprising the substance.

19. The method of claim 13, wherein determining the calibration value comprises determining via the following equation:

$$R0(t) = \frac{R1(t) \times (R1(Dt) - R2(0))}{R1(t) - R2(t)},$$

wherein R0(t) is the calibration value, R1(t) is each third sensor value at the third time, R1(Dt) is each first sensor value at the second time, R2(0) is each second sensor value at the second time, and R2(t) is each fourth sensor value at the third time.

20. A system for detecting a substance, the system comprising:
a first chemical sensor configured to provide sensor values responsive to a presence of the substance when the first chemical sensor is activated at a first time, wherein that the first chemical sensor is further configured to detect the substance when active;
a second chemical sensor configured to provide sensor values responsive to the presence of the substance when the second chemical sensor is activated at a second time that is subsequent to the first time, wherein the second chemical sensor is further configured to detect the substance when active; and
a processing device in operable communication with the first chemical sensor and the second chemical sensor, wherein the processing device is configured to:
determine a first sensor value associated with the first chemical sensor at the second time and a second sensor value associated with the second chemical sensor at the second time, wherein the first sensor value and the second sensor value are obtained at the second time;
determine a third sensor value associated with the first chemical sensor and a fourth sensor value associated with the second chemical sensor at a third time that is subsequent to the first time and the second time; and determine a calibration value based on the first sensor value, the second sensor value, the third sensor value, and the fourth sensor value.

21. The system of claim 20, wherein the first chemical sensor and the second chemical sensor each degrade over time with an exponential trajectory.

22. The system of claim 20, further comprising:
a first device comprising the first chemical sensor; and
a second device comprising the second chemical sensor.

23. The system of claim 20, further comprising:
a device comprising the first chemical sensor and the second chemical sensor.

24. The system of claim 20, wherein the substance comprises one or more of the following: ammonia, arsine, butane, carbon monoxide, chlorine gas, chlorine dioxide, chloroethane, dibrorane, diisopropyl methylphosphonate, dimethyl methylphosphonate, ethylene oxide, formaldehyde, heptaflouropropane, hydrogen, hydrogen chloride, hydrogen cyanide, hydrogen fluoride, hydrogen peroxide, hydrogen sulfide, methyl salicylate, natural gas, nitric oxide, nitrogen dioxide, ozone, phosgene, propane, radon, sulfur dioxide, sulfur hexafluoride, and vinyl chlorine.

25. The system of claim 20, wherein the first chemical sensor is further configured to provide sensor values responsive to the presence of the substance in the atmosphere surrounding the system.

26. The system of claim 20, wherein the first chemical sensor is further configured to provide sensor values responsive to the presence of the substance in a fluid.

27. The system of claim 20, wherein the processing device is configured to determine the calibration value via the following equation:

$$R0(t) = \frac{R1(t) \times (R1(Dt) - R2(0))}{R1(t) - R2(t)},$$

wherein R0(t) is the calibration value, R1(t) is the third sensor value at the third time, R1(Dt) is the first sensor value at the second time, R2(0) is the second sensor value at the second time, and R2(t) is the fourth sensor value at the third time.

28. The system of claim 20, wherein the second chemical sensor is further configured to provide sensor values responsive to the presence of the substance in the atmosphere surrounding the system.

29. The system of claim 20, wherein the second chemical sensor is further configured to provide sensor values responsive to the presence of the substance in a fluid.

* * * * *

UNITED STATES PATENT AND TRADEMARK OFFICE
CERTIFICATE OF CORRECTION

PATENT NO. : 8,869,586 B2  
APPLICATION NO. : 13/512799  
DATED : October 28, 2014  
INVENTOR(S) : Margalit Page 1 of 1

It is certified that error appears in the above-identified patent and that said Letters Patent is hereby corrected as shown below:

In the Specification,

In Column 1, Line 54, delete "time,." and insert -- time, --, therefor.

In Column 1, Line 58, delete "the first" and insert -- a first --, therefor.

In Column 2, Line 16, delete "there" and insert -- where --, therefor.

In Column 2, Line 17, delete "value values" and insert -- values --, therefor.

In Column 2, Line 32, delete "of the of the" and insert -- of the --, therefor.

In Column 2, Line 56, delete "determining" and insert -- determine --, therefor.

In Column 3, Line 34, delete "more values" and insert -- more sensor values --, therefor.

In Column 3, Line 40, delete "determining" and insert -- determine --, therefor.

In Column 4, Line 36, delete "$R1-R2=e^{-t}e^{-Dt}-e^{-t}=e^{-t}(e^{-DT}-1).$" and insert -- $R1-R2=e^{-t}e^{-Dt}-e^{-t}=e^{-t}(e^{-Dt}-1).$ --, therefor.

In Column 4, Line 38, delete "$A=e^{-DT}-1.$" and insert -- $A=e^{-Dt}-1.$ --, therefor.

In Column 4, Line 46, delete "R1(t)=R0(t)*(t)," and insert -- $R1(t) = R0(t)*f(t)$, --, therefor.

In the Claims,

In Column 10, Line 36, in Claim 1, delete "by processing" and insert -- by the processing --, therefor.

In Column 11, Line 62, in Claim 13, delete "of the of the" and insert -- of the --, therefor.

Signed and Sealed this  
Twenty-first Day of July, 2015

Michelle K. Lee  
*Director of the United States Patent and Trademark Office*